US008234909B2

(12) United States Patent
Suman et al.

(10) Patent No.: US 8,234,909 B2
(45) Date of Patent: Aug. 7, 2012

(54) METHOD AND APPARATUS FOR INSPECTING CERAMIC WALL FLOW FILTERS

(75) Inventors: Balram Suman, Painted Post, NY (US); Srinivasa Rao Vaddiraju, Corning, NY (US); Wei Xu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 497 days.

(21) Appl. No.: 12/548,057

(22) Filed: Aug. 26, 2009

(65) Prior Publication Data

US 2011/0048109 A1    Mar. 3, 2011

(51) Int. Cl.
*G01N 15/08* (2006.01)
(52) U.S. Cl. ............... 73/38; 73/40; 55/523; 95/273; 96/414; 96/417
(58) Field of Classification Search .............. 73/865.8, 73/38; 96/414–423
See application file for complete search history.

(56) References Cited

U.S. PATENT DOCUMENTS

| | | | |
|---|---|---|---|
| 3,441,381 A | 4/1969 | Keith et al. | |
| 3,780,772 A | 12/1973 | Carnanhan et al. | |
| 4,055,075 A | 10/1977 | Allan et al. | |
| 4,319,840 A | 3/1982 | Kondo et al. | |
| 4,515,007 A | 5/1985 | Herman | |
| 4,619,136 A | 10/1986 | Ortiz | |
| 4,676,092 A | 6/1987 | Tuttle | |
| 5,102,434 A | 4/1992 | Hijikata et al. | |
| 5,205,156 A | 4/1993 | Asano et al. | |
| 5,398,541 A | 3/1995 | Hijikata et al. | |
| 5,640,236 A | 6/1997 | Nagashima | |
| 6,666,070 B1 * | 12/2003 | Hagg et al. | 73/38 |
| 7,283,224 B1 | 10/2007 | Smithgall | |
| 7,410,528 B2 * | 8/2008 | Rae et al. | 95/273 |
| 7,520,918 B2 * | 4/2009 | Zoeller, III | 95/273 |
| 7,614,304 B2 * | 11/2009 | Gunasekaran et al. | 73/598 |
| 2003/0112437 A1 | 6/2003 | Enomoto et al. | |
| 2004/0000186 A1 | 1/2004 | Hagg et al. | |
| 2007/0022724 A1 | 2/2007 | Gargano et al. | |
| 2007/0238191 A1 | 10/2007 | Gargano et al. | |
| 2008/0173071 A1 | 7/2008 | Park et al. | |

FOREIGN PATENT DOCUMENTS

| | | |
|---|---|---|
| EP | 0 539 202 | 4/1993 |
| EP | 1 296 125 | 3/2003 |
| JP | 10202279 | 8/1998 |
| JP | 2000171024 | 6/2000 |
| JP | 2001165847 | 6/2001 |
| JP | 2004286703 | 10/2004 |
| WO | 2004/056448 | 8/2004 |

* cited by examiner

*Primary Examiner* — Hezron E Williams
*Assistant Examiner* — Hoang Nguyen
(74) *Attorney, Agent, or Firm* — Joseph M. Homa; Matthew J. Mason

(57) ABSTRACT

Methods are disclosed for inspecting a cylindrical porous ceramic body by positioning a diffuser near, and spaced apart from, the first end of a ceramic body; flowing a tracer flow toward the diffuser, wherein a first portion of the tracer flow passes through the diffuser, and a second portion of the tracer flow does not pass through the diffuser, the first and second portions of the tracer flow then entering the first end of the ceramic body, wherein the average velocity of the first portion of the tracer flow entering the ceramic body $V_{AVG1}$ is lower than the average velocity of the second portion of the tracer flow entering the ceramic body $V_{AVG2}$; directing light toward the second end of the ceramic body; and detecting reflected light coming from a location proximate the second transverse face at the second end of the ceramic body.

20 Claims, 6 Drawing Sheets

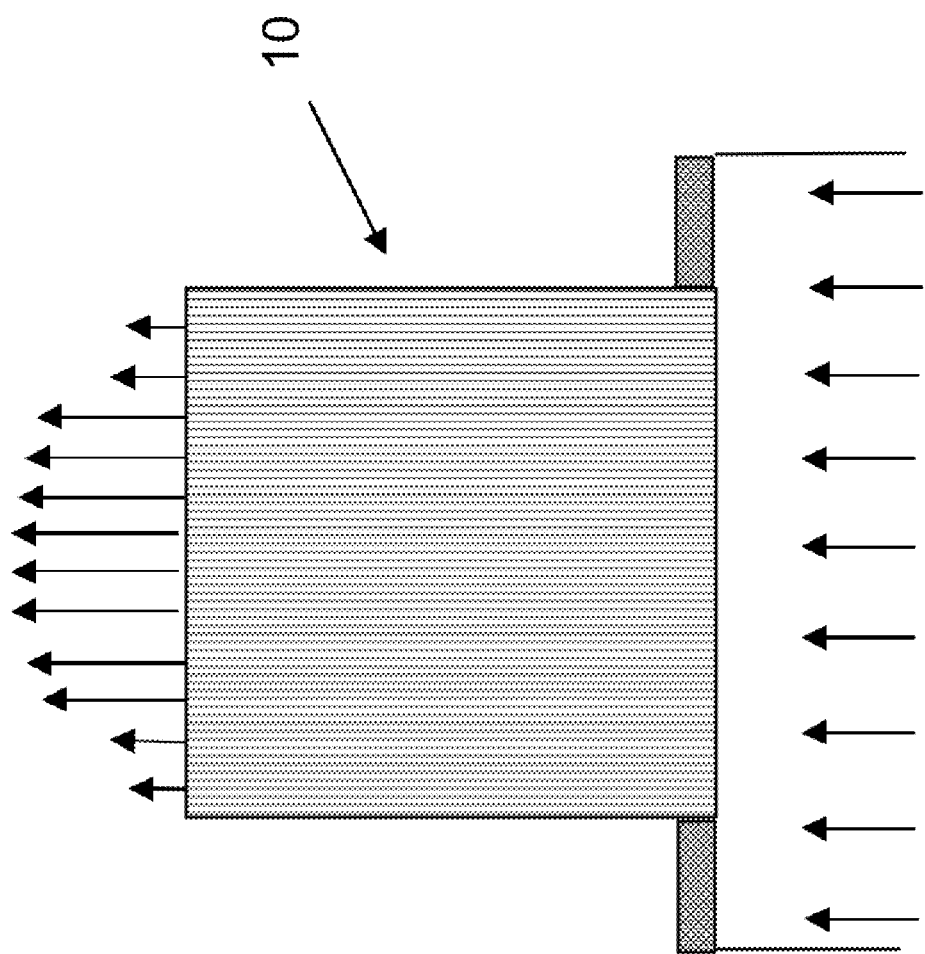

METHOD AND APPARATUS FOR INSPECTING CERAMIC WALL FLOW FILTERS

FIELD

The present invention relates to ceramic-based filters, and in particular relates to systems and methods of inspecting ceramic wall flow filters to check for any defects.

BACKGROUND

Ceramic bodies having internal honeycomb structures defined by porous walls have several uses, e.g., as particulate filter bodies. Such uses require selected channels of the structure to be sealed or plugged at one or both of the respective ends of the filter body.

In the operation of a ceramic plugged filter, a contaminated fluid or gas is brought under pressure to an inlet face and enters the ceramic filter body via those channels with open ends at the inlet face. Because these channels are sealed at the opposite (outlet) face, the contaminated fluid is forced through the thin porous walls into adjoining channels. The solid particulate contaminant in the fluid, which is too large to pass through the porous openings in the walls, is left behind, and a cleansed fluid exits the filter through the outlet channels.

Sealing the channels involves inserting a plugging material into the open ends of select channels, and subsequently drying the plugged filter. Plugging methods can potentially lead to defects, such as holes or fissures, in the plugs, which cause filter leaks. The channel walls of the honeycomb structure can contain defects, such as holes or fissures. It is therefore important in the filter manufacturing process to be able to quickly and efficiently inspect the ceramic filter bodies for defects that could ultimately cause leaks in the subsequently formed filter.

SUMMARY

One aspect of the invention is a method of inspecting a cylindrical porous ceramic body disposed about a first longitudinal axis and comprising a plurality of walls defining a plurality of channels extending axially in a longitudinal direction parallel to the first longitudinal axis, the ceramic body having opposing first and second ends, and first and second transverse faces disposed at the first and second ends, respectively, the ceramic body comprising at least one channel being open at the first end and being closed (plugged or otherwise sealed) at the second end and at least one adjacent channel being open at the second end, the method comprising: positioning a diffuser near, and spaced apart from, the first end of the ceramic body; flowing a tracer flow toward the diffuser, wherein a first portion of the tracer flow passes through the interior cavity of the diffuser, and a second portion of the tracer flow passes around or over the exterior of the diffuser, the first and second portions of the tracer flow then entering the first end of the ceramic body, wherein the average velocity of the first portion of the tracer flow entering the ceramic body $V_{AVG1}$ is lower than the average velocity of the second portion of the tracer flow entering the ceramic body $V_{AVG2}$; directing light toward the second end of the ceramic body; and detecting reflected light coming from a location proximate the second transverse face at the second end of the ceramic body.

The method disclosed herein helps to detect defects or leakages in filters by providing sufficient flow through the filter body, particularly at the periphery, in a rapid and economical manner.

These and other advantages of the invention will be further understood and appreciated by those skilled in the art by reference to the following written specification, claims and appended drawings.

BRIEF DESCRIPTION OF THE DRAWINGS

FIG. 6 schematically illustrates air flow into a ceramic honeycomb body without the diffuser.

DETAILED DESCRIPTION

Figure 1:
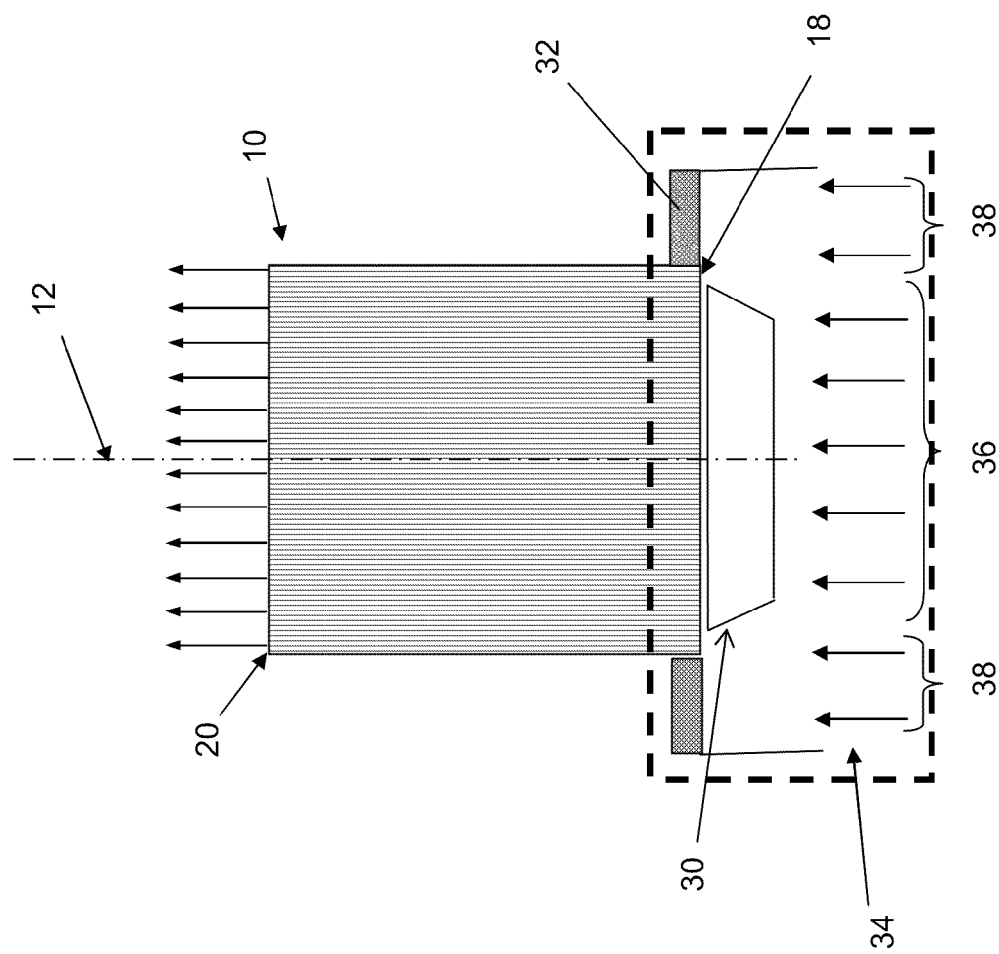
FIG. 1 is a schematic illustration of an elevational cutaway view of an embodiment of the method disclosed herein.

Reference is now made in detail to the present example embodiments of the invention, examples of which are illustrated in the accompanying drawings. Whenever possible, the same or similar reference numbers and symbols are used throughout the drawings to refer to the same or similar parts.

FIGS. 1-4 illustrate the methods and apparatuses disclosed herein, and schematically show a cylindrical porous ceramic body 10 disposed about a first longitudinal axis 12 and comprising a plurality of walls 14 defining a plurality of channels 16 extending axially in a longitudinal direction parallel to the first longitudinal axis 12. The ceramic body 10 has opposing first and second ends 18, 20, and first and second transverse faces disposed at the first and second ends, respectively, the ceramic body comprising at least one channel being open at the first end and being closed, i.e. plugged or otherwise sealed, such as by plugs 22 at the second end and at least one adjacent channel being open at the second end. A diffuser 30 is positioned near, and spaced apart from, the first end 18 of the ceramic body 10. A holder 32, such as a bladder ring, holds the ceramic body 10 in place, yet is releasable without damaging the ceramic body. In some embodiments, the holder 32 forms a gas-tight seal around the periphery of the ceramic body. A tracer flow 34 is flowed toward the diffuser 30, wherein a first portion 36 of the tracer flow 34 passes through the interior cavity of the diffuser 30, and a second portion 38 of the tracer flow passes around or over the exterior of the diffuser. The first and second portions 36, 38 of the tracer flow 34 then enter the first end 18 of the ceramic body 10, wherein the average velocity of the first portion 36 of the tracer flow 34 entering the ceramic body ($V_{AVG1}$) is lower than the average velocity of the second portion 38 of the tracer flow 34 entering the ceramic body ($V_{AVG2}$). Light is directed toward the second end 20 of the ceramic body 10 preferably from the side i.e. at an angle with respect to the first longitudinal axis 12. Reflected light coming from a location proximate the second transverse face at the second end 20 of the ceramic body 10 is detected; for example, fluid flow velocities are detected at a location proximate the second transverse face at the second end 20 of the ceramic body 10. As shown schematically in FIG. 4, in the event that a defect is present, for example a hole or fissure in a wall, more tracer fluid will flow into an adjacent channel and cause the exiting velocity to be higher than exiting velocities associated with surrounding cells which are not influenced by a defect.

The tracer flow 34 can be a solution, a mixture, a suspension, or combinations thereof. The suspension can be, for example, an aerosol, a vapor, a fog, a mist, a smoke, or combinations thereof. The tracer flow can comprise a tracer material and a carrier fluid. The carrier fluid can be a gas, a liquid, and combinations thereof.

At least part of the tracer flow 34 can be generated by a nebulizer or atomizer. The tracer flow can be comprised of a first material in liquid droplet form, or vapor form, or a combination thereof. The tracer flow can further comprise a carrier gas, such as air or nitrogen. In some embodiments, the tracer flow is a suspension comprised of an aerosol, a vapor, a fog, a mist, a smoke, or combinations thereof, in some embodiments, the suspension further comprises a carrier gas, such as air or nitrogen; in some embodiments, the tracer flow is air flow and fog (water vapor and/or droplets).

Figure 2:
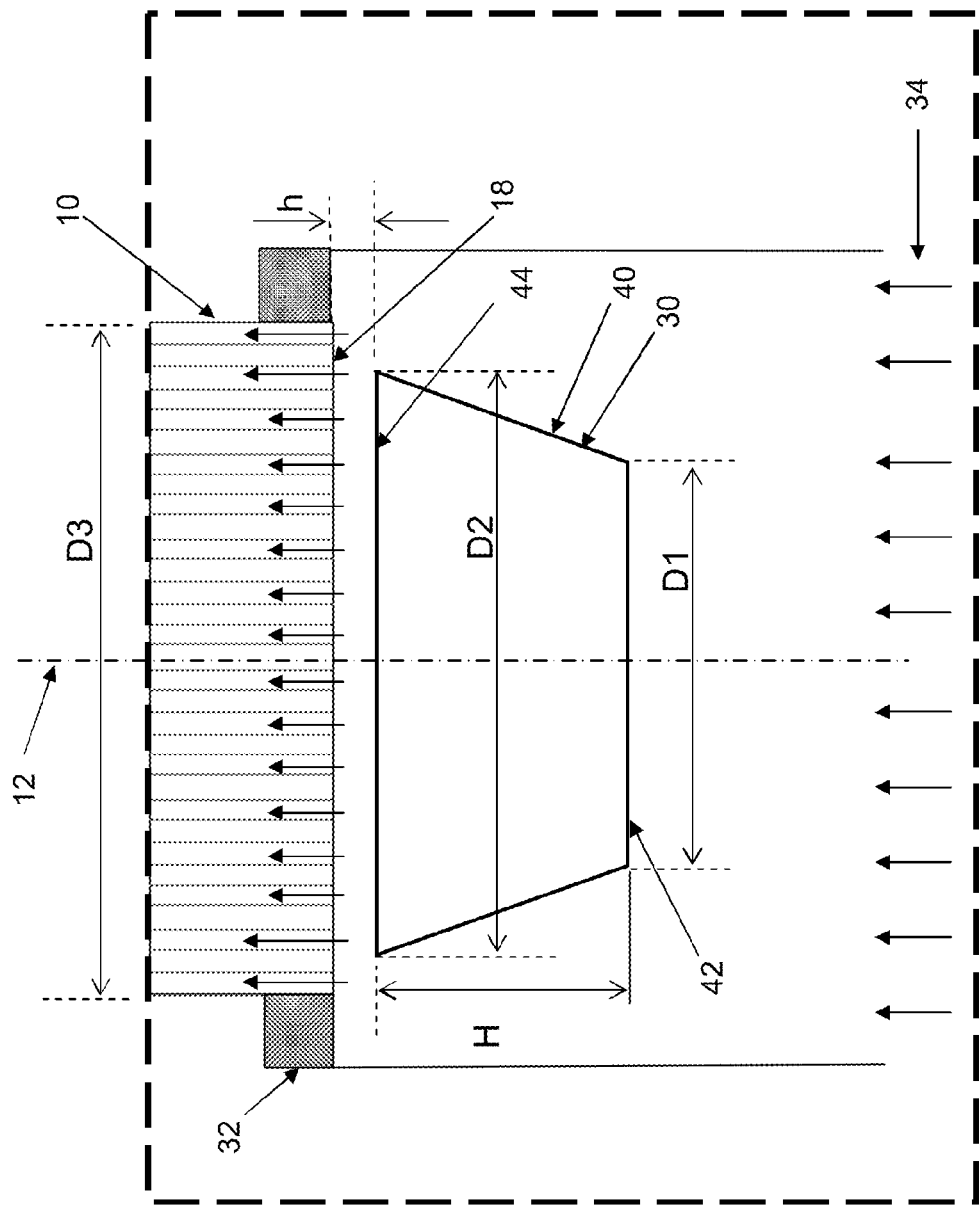
FIG. 2 is a schematic close-up of a portion of FIG. 1.
Figure 3:
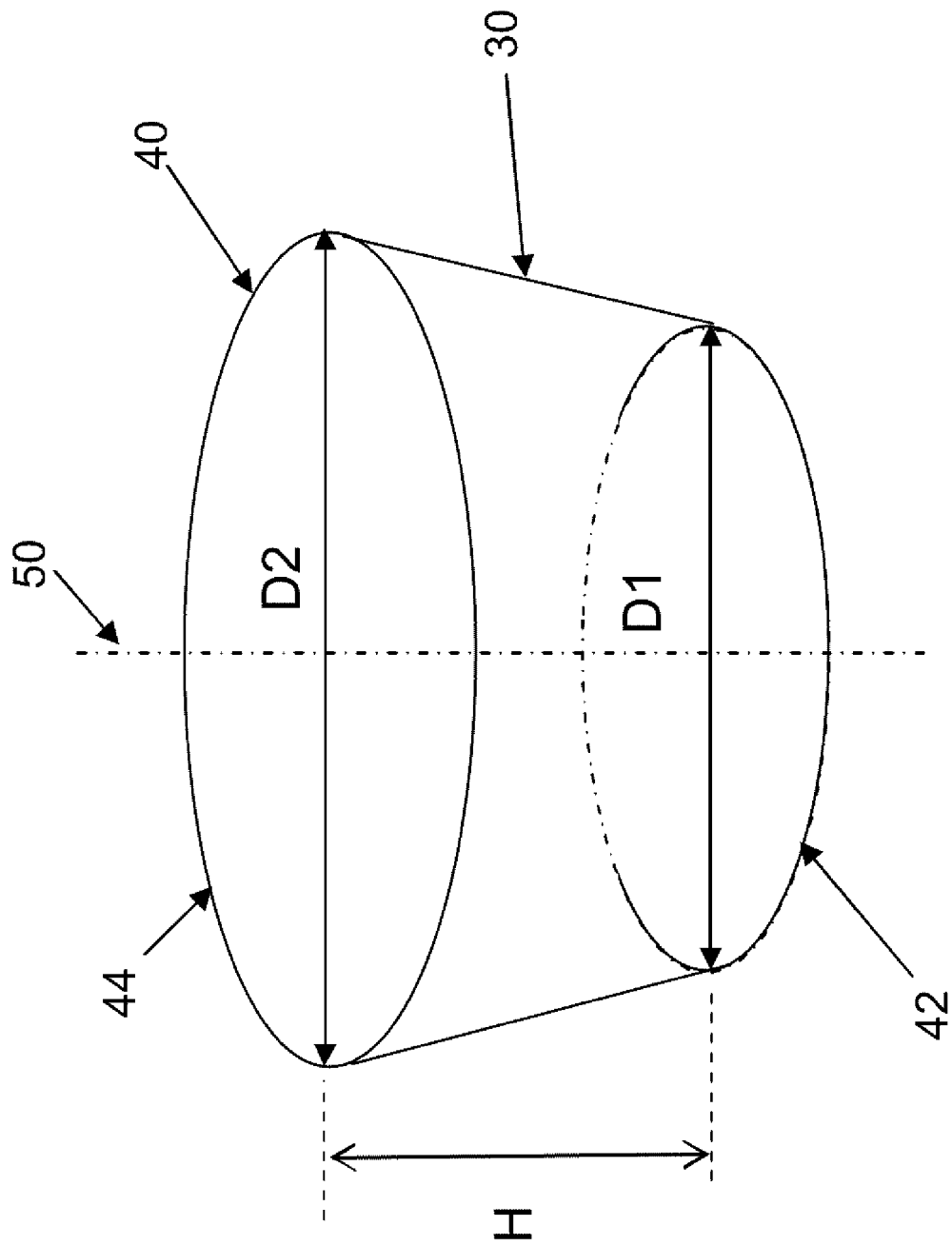
FIG. 3 is a schematic illustration of a perspective view of the diffuser of FIGS. 1 and 2.
Figure 4:
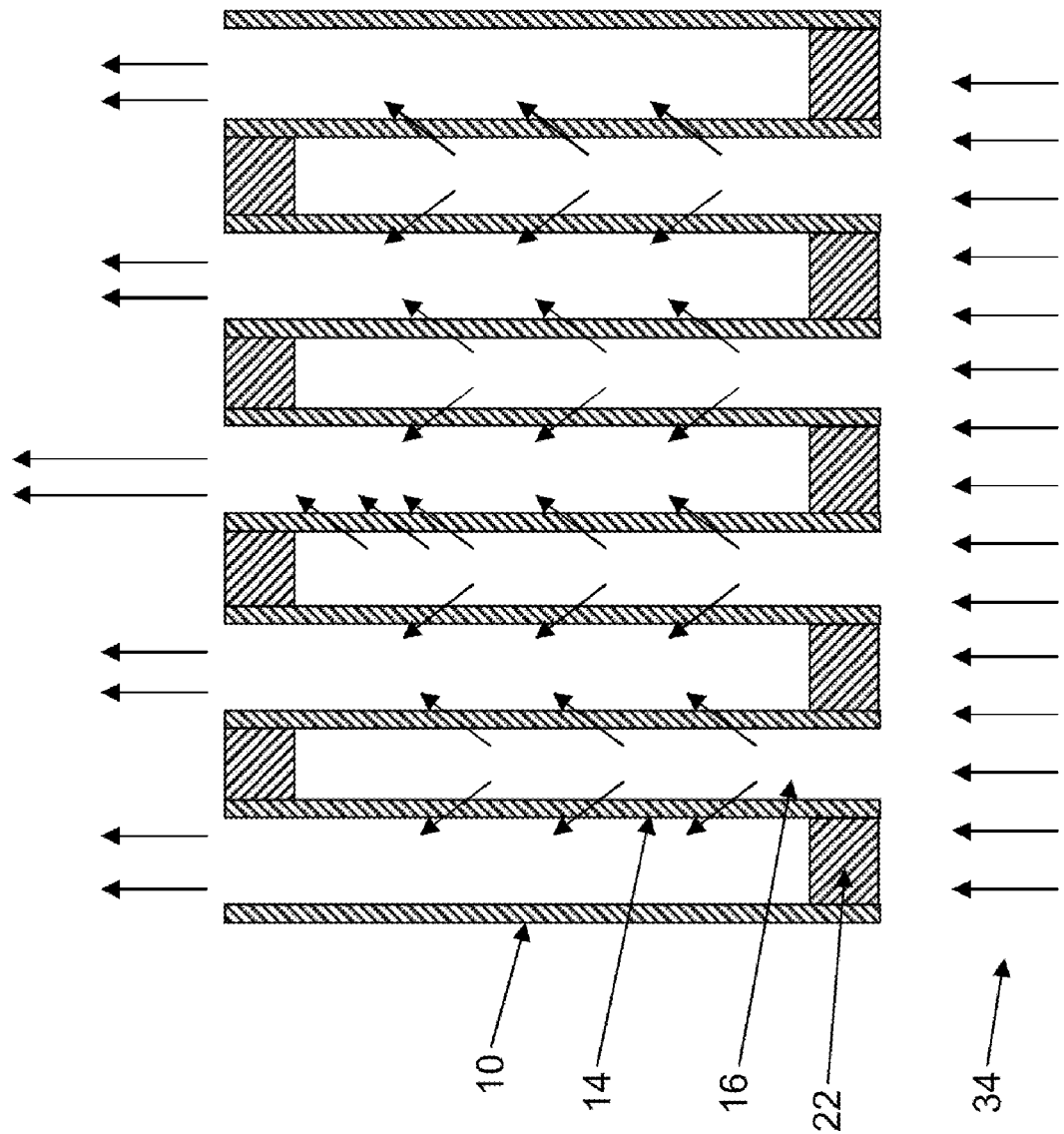
FIG. 4 is a schematic diagram of a flow entering open channels of a representative honeycomb filter body, the flow passing through the porous ceramic walls, and exiting the other end of the filter body.

As seen in the embodiment in FIGS. 1-3, the diffuser 30 comprises a diffuser wall 40 extending between first and second ends 42, 44, the second end 44 of the diffuser 30 being disposed proximate the first end 18 of the body 10, the first end 42 of the diffuser 30 being disposed farther away from the first end 18 of the body 10 than the second end 44 of the diffuser 30 is disposed away from the first end 18 of the body 30, the diffuser wall 40 defining first and second openings at the first and second ends 42, 44, respectively, having first and second hydraulic diameters, respectively, the second hydraulic diameter (D2) being greater than the first hydraulic diameter (D1). In some embodiments, the ratio D1/D2 is between 0.7 and 0.95, inclusive. In some embodiments, the first transverse face at the first end 18 of the body 10 has a third hydraulic diameter (D3), and the ratio D2/D3 is between 0.7 and 0.95, inclusive.

In some embodiments, the second end 44 of the diffuser 30 is disposed proximate the first end 18 of the ceramic body 10, but spaced apart therefrom. In some embodiments, the second end 44 of the diffuser 30 is spaced apart from the first end 18 of the ceramic body 10 by a spacing distance, h, and the diffuser has an axial length, H, and the ratio h/H is between 0.05 and 0.5. In some embodiments, H is between 1.0 inch and 5.0 inches, inclusive, and h is greater than 0 and less than 2.0 inches.

In some embodiments, the diffuser 30 and the tracer flow 34 are selected to provide a maximum flow velocity exiting the second transverse face of between 0.005 and 0.05 m/s.

In some embodiments, the first transverse face at first end 18 of the ceramic body has a first body peripheral contour of a first shape, and the diffuser wall 40 at the second end of the diffuser has a second body peripheral contour of a second shape. In some embodiments, at least one of the first and second shapes is circular, oval, or polygonal; in some embodiments, at least one of the first and second shapes is circular, oval, square, rectangular, or hexagonal. In some embodiments, the first and second shapes are the same.

In some embodiments, the directing of light toward the second end of the ceramic body 10 comprises transmitting laser light to a scan region proximate the second transverse face at the second end 20 of the ceramic body 10. In some embodiments, at least a portion of the laser light lies within a plane spaced away from the second transverse face. In some embodiments, an image signal is generated corresponding to the scanned region, in some embodiments, the image signal is generated via a vision system. The image signal can be analyzed to determine if one or more defects exist within the body.

The diffuser 30 can be disposed about a second longitudinal axis 50 which is parallel or substantially parallel to the first longitudinal axis 12. In some embodiments, the second longitudinal axis 50 is coincident with the first longitudinal axis 12.

The first portion 36 of the tracer flow 34 passes into the first end 42 of the diffuser 30, through the diffuser, and out of the second end 44 of the diffuser, into the first end 18 of the body 10, through the body, and out of the second end 20 of the body.

The second portion 38 of the tracer flow 34 passes outside of the diffuser 30, and generally flows past or along an exterior of the diffuser wall 40, into the first end 18 of the body 10, through the body, and out of the second end 20 of the body 10.

In some embodiments, the second portion 38 of the tracer flow 34 enters the first end 18 of the body 10 radially outward of the first portion 36 of the tracer flow 34 entering the first end 18 of the body.

In some embodiments, $V_{AVG2}/V_{AVG1}$ is greater than 1.1, and in other embodiments greater than 1.2.

In some embodiments, the plurality of walls 14 is configured as a matrix of intersecting walls. The matrix of intersecting walls can be arranged to form a honeycomb; the honeycomb can comprise cells having one or more cross-sectional contours selected from the group consisting of square, rectangular, hexagonal, pentagonal, heptagonal, octagonal, triangular, circular, and oval. In some embodiments, the matrix is surrounded by a non-porous peripheral wall.

EXAMPLE

Figure 5:
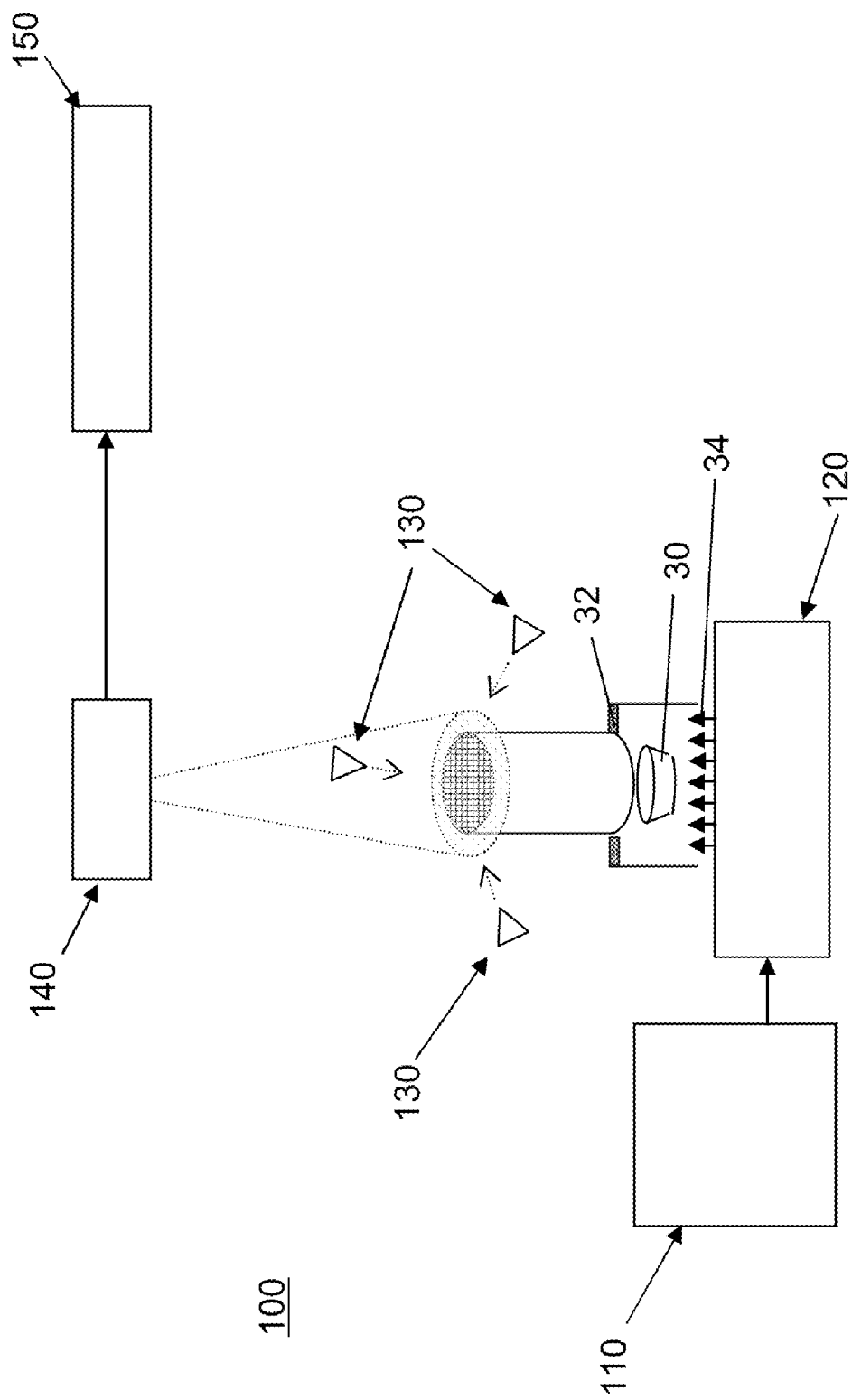
FIG. 5 is a schematic representation of an apparatus for effecting the methods disclosed herein.

FIG. 5 schematically illustrates an embodiment of an apparatus 100 for inspecting honeycomb porous ceramic filter bodies. Water is pumped by a water pump 110 to a nebulizer 120 and heated and converted into fog. The pressure in the nebulizer is high enough to force the fog to pass through the diffuser 30 and the filter 10. More fog will pass through regions of the filter that may contain defects or leakages than the regions without defects or leakages, where the fog flows through filter walls with porosity effect. The exiting fog is illuminated by high power laser beams 130 and a camera 140 takes a picture of the ceramic body 10, or the region in proximity to the second end 20 of the ceramic body, i.e. at the outlet of the tracer fog flow. The integrity of the filter can then be assessed based on analysis of the image. For example, the flow rate of fog in the regions with defects or leakages is high and the fog is illuminated more brightly with the camera, i.e. the filter has leaks and suggests that the filter is not acceptable for use. As the outlet flow rate is used to detect the quality of the filter, the flow rate is preferably uniform or nearly uniform at the outlet of the filter, and at least sufficient flow rate near the periphery can be used to check for leaks in the filter. The images may be viewed on the camera or transmitted to a vision system 150 for further viewing, magnification, analysis, or storage.

The apparatus disclosed herein has a smaller open area at the end where the fog enters the diffuser, and a larger open area at the opposite end of the diffuser so that the fog flowing through the diffuser stays inside the diffuser and the fog outside the diffuser stays outside the diffuser, resulting in more fog being forced to flow through the periphery of the ceramic body as compared to the inner portion of the body. Thus, an enhanced flow toward the periphery of body helps particularly in the detection of peripheral defects and leakages associated with the bodies.

FIG. 6 schematically illustrates air flow into a ceramic honeycomb body without the diffuser of the present disclosure. The air flow out of the honeycomb body does not uniformly exit the second end of the filter body.

What is claimed is:

1. A method of inspecting a cylindrical porous ceramic body disposed about a first longitudinal axis and comprising a plurality of walls defining a plurality of channels extending axially in a longitudinal direction parallel to the first longitudinal axis, the ceramic body having opposing first and second ends, and first and second transverse faces disposed at the first and second ends, respectively, the ceramic body comprising at least one channel being open at the first end and being closed at the second end and at least one adjacent channel being open at the second end, the method comprising:
   positioning a diffuser near, and spaced apart from, the first end of the ceramic body;
   flowing a tracer flow toward the diffuser, wherein a first portion of the tracer flow passes through the diffuser, and a second portion of the tracer flow does not pass through the diffuser, the first and second portions of the tracer flow then entering the first end of the ceramic body, wherein the average velocity of the first portion of the tracer flow entering the ceramic body $V_{AVG1}$ is lower than the average velocity of the second portion of the tracer flow entering the ceramic body $V_{AVG2}$;
   directing light toward the second end of the ceramic body; and
   detecting reflected light coming from a location proximate the second transverse face at the second end of the ceramic body.

2. The method of claim 1 further comprising detecting fluid flow velocities at a location proximate the second transverse face at the second end of the ceramic body.

3. The method of claim 2, wherein the fluid is selected from a group consisting of a solution, a mixture, a suspension, and combinations thereof.

4. The method of claim 3, wherein the suspension is selected from a group consisting of an aerosol, a vapor, a fog, a mist, a smoke, and combinations thereof.

5. The method of claim 3 wherein at least part of the tracer flow is generated by a nebulizer or atomizer.

6. The method of claim 1 wherein the diffuser comprises a diffuser wall extending between first and second ends, the second end of the diffuser being disposed proximate the first end of the body, the first end of the diffuser being disposed farther away from the first end of the body than the second end of the diffuser is disposed away from the first end of the body, the diffuser wall defining first and second openings at the first and second ends, respectively, having first and second hydraulic diameters, respectively, the second hydraulic diameter (D2) being greater than the first hydraulic diameter (D1).

7. The method of claim 6 wherein the ratio D1/D2 is between 0.7 and 0.95, inclusive.

8. The method of claim 6 wherein the first transverse face has a third hydraulic diameter (D3), and the ratio D2/D3 is between 0.7 and 0.95, inclusive.

9. The method of claim 1 wherein the second end of the diffuser is disposed proximate the first end of the ceramic body.

10. The method of claim 9 wherein the second end of the diffuser is spaced apart from the first end of the ceramic body by a spacing distance, h, and the diffuser has an axial length, H, and the ratio h/H is between 0.05 and 0.5.

11. The method of claim 10 wherein H is between 1 inch and 5 inches, inclusive, and h is greater than 0 and less than 2.0 inches.

12. The method of claim 1 wherein the diffuser and the tracer flow are selected to provide a maximum flow velocity exiting the second transverse face of between 0.005 and 0.05 m/s.

13. The method of claim 1 wherein the directing of light toward the second end of the ceramic body comprises transmitting laser light to a scan region proximate the second transverse face of the ceramic body.

14. The method of claim 1 wherein at least a portion of the laser light lies within a plane spaced away from the second transverse face.

15. The method of claim 1 wherein the diffuser is disposed about a second longitudinal axis which is parallel or substantially parallel to the first longitudinal axis.

16. The method of claim 1 wherein the first portion of the tracer flow passes into the first end of the diffuser, through the diffuser, and out of the second end of the diffuser, into the first end of the body, through the body, and out of the second end of the body.

17. The method of claim 1 wherein the second portion of the tracer flow passes outside of the diffuser, into the first end of the body, through the body, and out of the second end of the body.

18. The method of claim 1 wherein the second portion of the tracer flow enters the first end of the body radially outward of the first portion of the tracer flow entering the first end of the body.

19. The method of claim 1 wherein $V_{AVG2}/V_{AVG1}$ is greater than 1.1.

20. The method of claim 1 wherein the plurality of walls is configured as a matrix of intersecting walls.

* * * * *